(12) United States Patent
Schubert et al.

(10) Patent No.: US 8,603,225 B2
(45) Date of Patent: Dec. 10, 2013

(54) ALUMINUM NAPHTHALENEDICARBOXYLATE AS POROUS METAL-ORGANIC FRAMEWORK MATERIAL

(75) Inventors: Markus Schubert, Ludwigshafen (DE); Ulrich Mueller, Neustadt (DE); Stefan Marx, Zurich (CH); Christoph Kiener, Weisenheim am Sand (DE); James Reuben Brown, Mannheim (DE); Gerhard Krennrich, Frankenthal (DE)

(73) Assignee: BASF SE, Ludwigshafen (DE)

( * ) Notice: Subject to any disclaimer, the term of this patent is extended or adjusted under 35 U.S.C. 154(b) by 393 days.

(21) Appl. No.: 12/447,671

(22) PCT Filed: Oct. 24, 2007

(86) PCT No.: PCT/EP2007/061386
§ 371 (c)(1),
(2), (4) Date: Apr. 29, 2009

(87) PCT Pub. No.: WO2008/052916
PCT Pub. Date: May 8, 2008

(65) Prior Publication Data
US 2010/0064888 A1  Mar. 18, 2010

(30) Foreign Application Priority Data
Oct. 30, 2006 (EP) ..................................... 06123200

(51) Int. Cl.
*B01D 53/02* (2006.01)
(52) U.S. Cl.
USPC .............. 95/139; 95/900; 96/108; 428/304.4; 556/170; 502/401
(58) Field of Classification Search
USPC .......... 95/139; 428/304.4; 556/170; 134/6, 7; 210/660, 690
See application file for complete search history.

(56) References Cited

U.S. PATENT DOCUMENTS

| | | | |
|---|---|---|---|
| 5,648,508 A | * | 7/1997 | Yaghi ................................. 556/9 |
| 6,929,679 B2 | | 8/2005 | Müller et al. |

(Continued)

FOREIGN PATENT DOCUMENTS

| | | |
|---|---|---|
| DE | 10 2005 000 938 A1 | 7/2006 |
| DE | 10 2005 012 087 A1 | 9/2006 |

(Continued)

OTHER PUBLICATIONS

U.S. Appl. No. 12/594,604, filed Oct. 5, 2009, Stein, et al.

(Continued)

*Primary Examiner* — Duane Smith
*Assistant Examiner* — Christopher P Jones
(74) *Attorney, Agent, or Firm* — Oblon, Spivak, McClelland, Maier & Neustadt, L.L.P.

(57) ABSTRACT

The present invention relates to a porous metal-organic framework material comprising a bidentate organic compound bound by coordination to a metal ion, the metal ion being $Al^{III}$ and the bidentate organic compound being 2,6-naphthalenedicarboxylate, wherein the X-ray diffractogram (XRD) of the framework material has a first reflection in the range from $6.5°<2\Theta<7.5°$ and a second reflection in the range from $13.8°<2\Theta<15.0°$, the area of the first reflection being greatest in relation to the area of all reflections in the range from $2°<2\Theta<70°$ and the area of the second reflection being second greatest, and the sum of the areas of the first and second reflections giving at least 50% in relation to the total area of all reflections in the range from $2°<2\Theta<70°$. The invention further relates to shaped bodies comprising such a framework material, processes for production of the framework material and also to the use of the framework material or of the proposed shaped body.

17 Claims, 4 Drawing Sheets

(56) References Cited

U.S. PATENT DOCUMENTS

| | | |
|---|---|---|
| 2003/0148165 A1 | 8/2003 | Muller et al. |
| 2004/0081611 A1 | 4/2004 | Muller et al. |
| 2006/0210458 A1 | 9/2006 | Mueller et al. |
| 2007/0227898 A1 | 10/2007 | Muller et al. |
| 2007/0248852 A1 | 10/2007 | Mueller et al. |
| 2008/0190289 A1 | 8/2008 | Muller et al. |

FOREIGN PATENT DOCUMENTS

| | | |
|---|---|---|
| DE | 10 2005 022 844 A1 | 11/2006 |
| EP | 0 102 544 B1 | 3/1984 |
| EP | 0 592 050 A1 | 4/1994 |
| EP | 1 674 555 A1 | 6/2006 |
| EP | 1 702 925 A1 | 9/2006 |
| JP | 59-155333 | 9/1984 |
| JP | 3037156 | 4/1988 |
| WO | WO 94/13584 | 6/1994 |
| WO | WO 94/29408 | 12/1994 |
| WO | WO 03/035717 A1 | 5/2003 |
| WO | WO 03/064030 A1 | 8/2003 |
| WO | WO 03/101975 A1 | 12/2003 |
| WO | WO 03/102000 A1 | 12/2003 |
| WO | WO 2004/037895 A1 | 5/2004 |
| WO | WO 2005/003069 A2 | 1/2005 |
| WO | WO 2005/003622 A1 | 1/2005 |
| WO | WO 2005/049484 A1 | 6/2005 |
| WO | WO 2005/049892 A1 | 6/2005 |
| WO | WO 2006/072573 A2 | 7/2006 |
| WO | WO 2006/089908 A1 | 8/2006 |
| WO | WO 2007/023134 A1 | 3/2007 |
| WO | WO 2007/131948 A2 | 11/2007 |

OTHER PUBLICATIONS

U.S. Appl. No. 12/597,616, filed Oct. 26, 2009, Schubert, et al.
U.S. Appl. No. 12/601,022, filed Nov. 20, 2009, Schubert, et al.
U.S. Appl. No. 12/600,539, filed Nov. 17, 2009, Schubert, et al.
Thierry Loiseau, et al., "A Rationale for the Large Breathing of the Porous Aluminum Terephthalate (MIL-53) Upon Hydration", Chem. Eur. J., vol. 10, No. 6, XP002456416, Mar. 15, 2004 , pp. 1373-1382.
Thierry Loiseau, et al., "Hydrothermal Synthesis and Crystal Structure of a New Three-Dimensional Aluminum-Organic Framework MIL-69 with 2,6-naphthalenedicarboxylate (ndc), Al(OH)(ndc)•$H_2O$",C.R. Chimie, vol. 8, No. 3-4, Mar. 2005, pp. 765-772.
Irena Senkovska, et al., "Solvent-Induced Pore-Size Adjustment in the Metal-Organic Framework [Mg3 (ndc)3 (dmf)4] (ndc=naphthalenedicarboxylate)", Eur. J. Inorg. Chem., XP-002467340, 2006, pp. 4564-4569.
Sandrine Bourrelly, et al., "Different Adsorption Behaviors of Methane and Carbon Dioxide in the Isotypic Nanoporous Metal Terephthalates MIL-53 and MIL-47", vol. 127, No. 39, XP-002467341, Sep. 13, 2005, pp. 13519-13521.
Helmut Wendeborn, et al., "Stüeckigmachen, Einleitung", Ullmanns Encyklopädie der Technischen Chemie, $4^{th}$ edition, vol. 2, 1972, pp. 313-343.
K.S.W. Sing, et al., "Reporting Physisorption Data for Gas/Solid Systems with Special Reference to the Determination of Surface Area and Porosity", Pure & Appl. Chem. 57, 1985, pp. 603-619.
U.S. Appl. No. 13/002,612, filed Jan. 4, 2011, Leung, et al.
U.S. Appl. No. 13/003,839, filed Jan. 12, 2011, Schubert, et al.
U.S. Appl. No. 12/668,436, filed Jan. 11, 2010, Schubert, et al.
U.S. Appl. No. 12/863,339, filed Jul. 16, 2010, Schubert, et al.

\* cited by examiner

ALUMINUM NAPHTHALENEDICARBOXYLATE AS POROUS METAL-ORGANIC FRAMEWORK MATERIAL

The present invention relates to a porous metal-organic framework material, shaped bodies comprising it, processes for producing the framework material and also to the use of said framework material or shaped body for storage, separation, controlled release, chemical reaction or as support.

Porous metal-organic framework materials are known in the prior art. They are distinguished, in particular, by their porosity and can frequently be supplied to applications comparable to those which are known of inorganic zeolites.

Metal-organic framework materials customarily comprise an at least bidentate organic compound bound by coordination to a metal ion and which, together with the metal ion, forms the framework of the metal-organic framework material.

A suitable choice of metal and/or organic compound makes possible optimization for the desired field of application. In this case, for example, the choice of organic compound can affect the pore distribution. In addition, the metal can make a contribution to adsorption processes.

There is therefore a constant requirement for providing special metal-organic framework materials which, in particular, have unusual properties which are due to the choice of the metal and also the organic compound.

As a metal of interest, aluminum may be mentioned, since owing to strong coordination bonds, comparatively robust metal-organic framework materials can be obtained. In addition, the $Al^{3+}$ ion, owing to its octahedral coordination, is suitable in principle for building up three-dimensional framework compounds. In addition, the aluminum salts which can be used as starting material are readily accessible and inexpensive.

As a bidentate organic compound of interest, mention may be made of 2,6-naphthalenedicarboxylic acid. On account of the naphthalene framework and also the position of the two carboxylic acid functionalities, the individual metal centers in the porous metal-organic framework material can be comparatively greatly spaced out, wherein, with the aid of the rigid naphthalene framework, the metal-organic framework material as such is likewise comparatively rigid and robust. 2,6-Naphthalenedicarboxylic acid itself is relatively chemically and thermally stable and, like the aluminum salts, is available in large quantities.

T. Loiseau et al., C. R. Chimie 8 (2005), 765-772 describe the hydrothermal synthesis and crystal structure of the three-dimensional aluminum-organic framework material "MIL-69", which is made up of aluminum ions and 2,6-naphthalenedicarboxylate. The crystal structure and also further physical properties of the framework material are studied here.

In this work a greatly distorted, but otherwise similar structure to "MIL-53" (aluminum terephthalate) is found for the "MIL-69" structure, but the water molecule typically incorporated in this structure can be removed without changing the structure.

A reproduction of the described framework material, however, yields relatively low specific surface areas, so that its suitability for applications such as storage or separation of gases is relatively low.

There is therefore a need for alternative aluminum naphthalenedicarboxylate framework materials which have superior properties in particular with respect to storage and separation of gases.

One object of the present invention is therefore the provision of such framework materials.

The object is achieved by a porous metal-organic framework material comprising a bidentate organic compound bound by coordination to a metal ion, the metal ion being $Al^{III}$ and the bidentate organic compound being 2,6-naphthalenedicarboxylate, wherein the X-ray diffractogram (XRD) of the framework material has a first reflection in the range from $6.5°<2\Theta<7.5°$ and a second reflection in the range from $13.8°<2\Theta<15.0°$, the area of the first reflection being greatest in relation to the area of all reflections in the range from $2°<2\Theta<70°$ and the area of the second reflection being second greatest, and the sum of the areas of the first and second reflections giving at least 50% in relation to the total area of all reflections in the range from $2°<2\Theta<70°$.

It has been found that by varying the production conditions it is possible to obtain a novel metal-organic framework material which is made up of aluminum ions and 2,6-naphthalenedicarboxylate like the structure "MIL-69" known in the prior art, but has an X-ray diffractogram different from this and furthermore has a comparatively high specific surface area.

It has been found, in particular here, that the selection of the weight fraction of the starting materials (aluminum and 2,6-naphthalenedicarboxylate) in relation to the total weight of the reaction mixture, so that it is less than a certain value, results in the novel structure.

As has already been mentioned above, the novel structure differs significantly in its X-ray diffractogram.

BRIEF DESCRIPTION OF THE DRAWINGS

Figure 1:
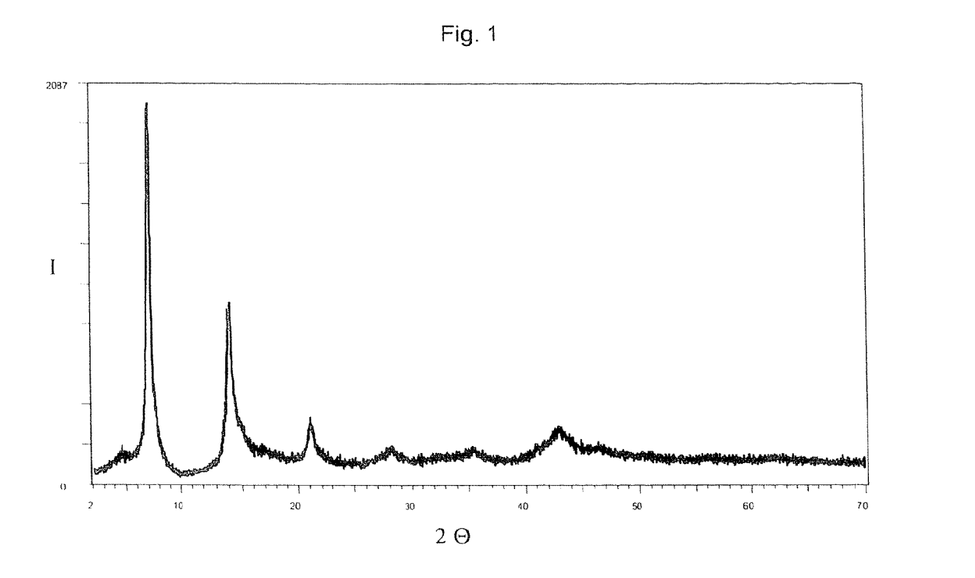
FIGS. 1 and 2 show X-ray diffractograms of porous metal-organic framework materials.

A more complete appreciation of the invention and many of the attendant advantages thereof will be readily obtained as the same become better understood by reference to the following detailed description when considered in connection with the accompanying drawings, wherein:

FIG. 1 shows the X-ray diffractogram of the porous metal-organic framework material of the invention. Here, as in all diffractograms shown in the drawings, the intensity I (Lin (Counts)) is shown as functions of the 2 theta scale ($2\Theta$).

Figure 2:
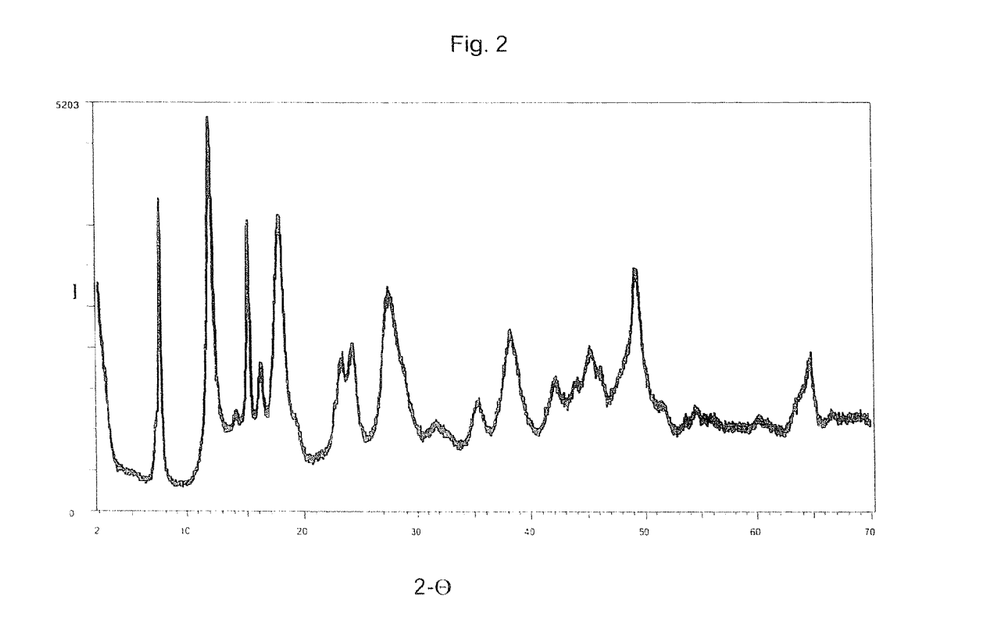

In contrast, FIG. 2 shows the framework structure "MIL-69" known from the prior art.

Figure 3:
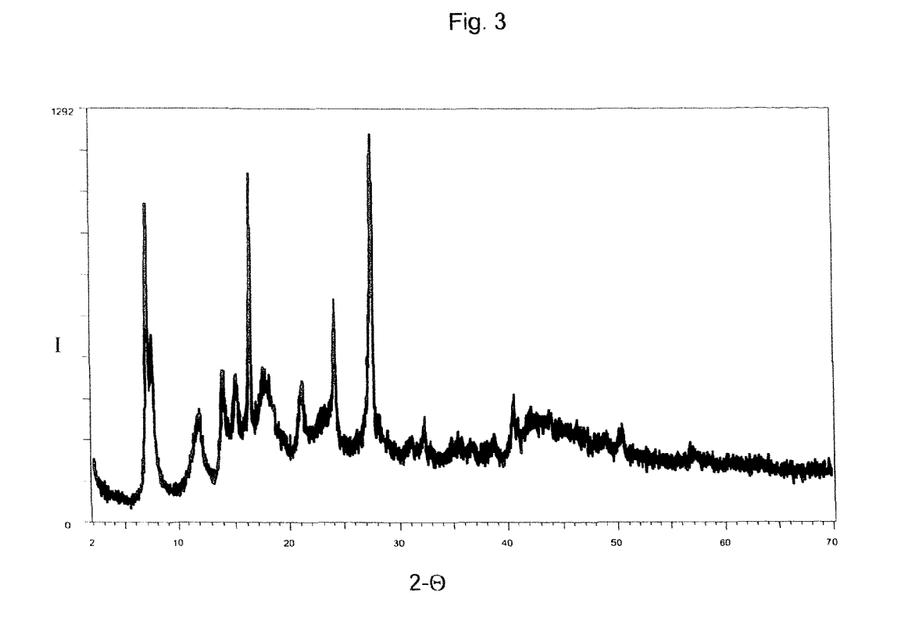
FIG. 3 shows an X-ray diffractogram of comparative example 2.

On the basis of the significantly differing X-ray diffractograms, the two structures can be differentiated from one another. It is equally possible that the porous metal-organic framework material of the invention is in a mixture with that from the prior art, in which case correspondingly a superimposition of the two diffractograms takes place. Such an example is shown in FIG. 3.

The structure of the porous metal-organic framework material of the invention can be recognized, in particular, from the fact that the X-ray diffractogram (XRD) has a first reflection in the range from $6.5°<2\Theta<7.5°$ and a second reflection in the range from $13.8°<2\Theta<15.0°$, with the area of the first reflection being greatest in relation to the area of all reflections in the range from $2°<2\Theta<70°$ and the area of the second reflection being the second greatest, and the sum of the areas of the first and second reflections giving at least 50% in relation to the total area of all reflections in the range from 2°<2Θ<70°.

Preferably, the first reflection is in the range from 6.7°<2Θ<7.3° and the second reflection in the range from 13.9°<2Θ<14.8°, in particular a range from 14.0°<2Θ<14.5°.

In this case the diffractogram can be determined as follows: the sample is installed as powder into the sample container of a commercially available instrument (Siemens D-5000 diffractometer or Bruker D8-Advance). The radiation source used is Cu—Kα-radiation having variable primary and secondary apertures and secondary monochromator. The signal is detected via a scintillation detector (Siemens) or Solex semiconductor detector (Bruker). The 2θ measurement range selected is typically between 2° and 70°. The angle step is 0.02°, the measurement time per angle step typically 2-4 s. In the analysis, reflections are differentiated from background noise by a signal strength which is at least 3-times higher. The area analysis can be performed manually by plotting a base line to the individual reflections. Alternatively, use can be made of programs such as, for example, "Topas-Profile" from Bruker, with the adaptation for background preferably being performed automatically via a first order polynomial in the software.

The structure of the framework material of the invention preferably has a one-dimensional channel structure in which linear chains of $Al^{III}$ ions and OH groups are bridged via the organic 2,5-naphthalenedicarboyxlate to give a three-dimensional orthorhombic structure, the aperture angle α (Al—Al—Al) being in the range from 78° to 90°, preferably in the range from 80° to 90°, more preferably 82.5°±1.5°, or 88.5°±1.5°.

In addition, the structure of the framework material of the invention has a lattice constant b (height of the unit cell) of 16 to 18.5 Å.

The metal-organic framework material of the invention can be present in pulverulent form or as agglomerate.

The porous metal-organic framework material of the invention can be used as such in powder form before it is converted into a shaped body.

Accordingly, a further aspect of the present invention is that the porous metal-organic framework material of the invention is present as powder.

A further aspect of the present invention is therefore a shaped body comprising the porous metal-organic framework material of the invention.

The production of shaped bodies from metal-organic framework materials is described, for example, in WO-A 03/102000.

Preferred processes for production of shaped bodies are in this case rod extrusion or tableting. In the shaped body production, the framework material can have further materials, such as, for example, binders, lubricants or other additives, which are added during production. It is equally conceivable that the framework material has further components such as, for example, absorbents such as activated carbon or the like.

Essentially no restrictions exist with respect to possible geometries of the shaped bodies. For example, those which may be mentioned are, inter alia, pellets such as, for example, disk-shaped pellets, pills, spheres, granules, extrudates such as, for example, rod extrudates, honeycombs, meshes or hollow bodies.

Essentially no restrictions exist with respect to possible geometries of the shaped bodies. For example, those which may be mentioned are, inter alia, pellets such as, for example, any disk shaped body or hollow article.

For production of these shaped bodies, in principle all suitable processes are possible. In particular, the following process procedures are preferred:

kneading/pan-grinding the framework material alone or together with at least one binder and/or at least one pasting agent and/or at least one template compound to obtain a mixture; shaping the resultant mixture by means of at least one suitable method such as, for example, extrusion; optionally washing and/or drying and/or calcination of the extrudate; optionally final-processing.

Tableting together with at least one binder and/or other auxiliary.

Applying the framework material to at least one if appropriate porous support material. The resultant material can then be further processed according to the above-described method to give a shaped body.

Applying the framework material to at least one if appropriate porous substrate.

Kneading/pan-grinding and shaping can proceed according to any suitable process such as described, for example, in Ullmanns Enzyklopädie der Technischen Chemie [Ullmann's Encyclopedia of Industrial Chemistry], 4th edition, volume 2, pp. 313ff (1972).

For example, the kneading/pan-grinding and/or shaping can proceed by means of a piston press, roller press in the presence or absence of at least one binder, compounding, pelleting, tableting, extruding, co-extruding, foaming, spinning, coating, granulation, preferably spray-granulation, spraying, spray-drying or a combination of two or more of these methods.

Very particularly preferably, pellets and/or tablets are produced.

Kneading and/or shaping can proceed at elevated temperatures such as, for example, in the range from room temperature to 300° C., and/or at elevated pressure such as, for example, in the range from atmospheric pressure up to a few hundred bar and/or in a protective gas atmosphere such as, for example, in the presence of at least one noble gas, nitrogen or a mixture of two or more thereof.

The kneading and/or shaping is carried out according to a further embodiment with addition of at least one binder, with as binder in principle any chemical compound being able to be used which ensures the viscosity of the mix to be kneaded and/or shaped which is required for kneading and/or shaping. Accordingly, binders within the meaning of the present invention can be not only viscosity-elevating compounds, but also viscosity-decreasing compounds.

As binders which are, inter alia, preferred, mention may be made of, for example, aluminum oxide or aluminum oxide-comprising binders, as are described, for example, in WO 94/29408, silicon dioxide, as described, for example, in EP 0 592 050 A1, mixtures of silicon dioxide and aluminum oxide, as are described, for example, in WO 94/13584, clay minerals, as are described, for example, in JP 03-037156 A, for example, montmorillonite, kaolin, bentonite, halloysite, dickite, nacrite and anauxite, alkoxysilanes as are described, for example, in EP 0 102 544 B1, for example, tetraalkoxysilanes such as, for example, tetramethoxysilane, tetraethoxysilane, tetrapropoxysilane, tetrabutoxysilane, or, for example, trialkoxysilanes, such as, for example, trimethoxysilane, triethoxysilane, tripropoxysilane, tributoxysilane, alkoxytitanates, for example, tetraalkoxytitanates, such as, for example, tetramethoxytitanate, tetraethoxytitanate, tetrapropoxytitanate, tetrabutoxytitanate, or, for example, trialkoxytitanates, such as, for example, trimethoxytitanate, triethoxytitanate, tripropoxytitanate, tributoxytitanate, alkoxyzirconates, for example, tetraalkoxyzirconates such as, for example, tetramethoxyzirconate, tetraethoxyzirconate, tetrapropoxyzirconate, tetrabutoxyzirconate, or, for example, trialkoxyzirconates such as, for example, trimethoxyzirconate, triethoxyzirconate, tripropoxyzirconate, tributoxyzirconate, silica sols, amphiphilic substances and/or graphites.

As viscosity-increasing compound, use can also be made, for example, if appropriate in addition to the abovementioned compounds, of an organic compound and/or a hydrophilic polymer such as, for example, cellulose or a cellulose derivative such as, for example, methylcellulose and/or a polyacrylate and/or a polymethacrylate and/or a poly(vinyl alcohol) and/or a polyvinylpyrrolidone and/or a polyisobutene and/or a polytetrahydrofuran and/or a poly(ethylene oxide).

As pasting agent, use can be made of inter alia preferably water or at least one alcohol such as, for example, a monohydric alcohol having 1 to 4 carbon atoms such as, for example, methanol, ethanol, n-propanol, isopropanol, 1-butanol, 2-butanol, 2-methyl-1-propanol or 2-methyl-2-propanol or a mixture of water and at least one of said alcohols or one polyhydric alcohol such as, for example, a glycol, preferably a water-miscible polyhydric alcohol, alone or as a mixture with water and/or at least one of said monohydric alcohols.

Further additives which can be used for the kneading and/or shaping are, inter alia amines or amine derivatives such as, for example, tetraalkylammonium compounds or aminoalcohols and carbonate-comprising compounds such as calcium carbonate for instance. Such further additives are described, for instance, in EP 0 389 041 A1, EP 0 200 260 A1 or WO 95/19222.

The sequence of the additives such as template compound, binder, pasting agent, viscosity-elevating substance, in the shaping and kneading is not critical in principle.

According to a further preferred embodiment, the shaped body obtained in accordance with kneading and/or shaping is subjected to at least one drying which is generally carried out at a temperature in the range from 25 to 500° C., preferably in the range from 50 to 500° C., and particularly preferably in the range from 100 to 350° C. It is equally possible to dry in vacuum or under a protecting gas atmosphere or by spray drying.

According to a particularly preferred embodiment, in the context of this drying process, at least one of the compounds added as additives is removed at least in part from the shaped body.

The metal-organic framework material of the invention comprises pores, in particular micropores and/or mesopores. Micropores are defined as those having a diameter of 2 nm or less and mesopores are defined by a diameter in the range from 2 to 50 nm (Pure & Appl. Chem. 57 (1985) 603-619). The presence of micropores and/or mesopores can be studied using sorption measurements, these measurements determining the sorption capacity of the metal-organic framework materials for nitrogen at 77 kelvin (according to Langmuir) as specified in DIN 66131 and/or DIN 66134.

Preferably, the pores are present in the form of one-dimensional channels having a diameter of greater than 10, but less than 25 angströms, particularly preferably from 15 to 20, in particular from 16 to 18 Å.

Preferably, the specific surface area, calculated in accordance with the Langmuir model (DIN 66131, 66134) for the metal-organic framework material of the invention in powder form is at least 1000 $m^2/g$, more preferably at least 1200 $m^2/g$, more preferably at least 1400 $m^2/g$, still more preferably at least 1600 $m^2/g$, still more preferably at least 1800 $m^2/g$ and particularly preferably at least 1950 $m^2/g$.

Shaped bodies made from the metal-organic framework material of the invention can have a lower specific surface area; preferably, however, at least 500 $m^2/g$, more preferably at least 600 $m^2/g$, still more preferably at least 700 $m^2/g$, in particular at least 800 $m^2/g$.

The present invention further relates to a process for producing a porous metal-organic framework material of the invention comprising the step reacting a reaction mixture comprising an aluminum compound, 2,6-naphthalenedicarboxylic acid or one of its salts and an organic solvent at temperatures in the range from 100° C. to 200° C. with stirring, the sum of the fractions of the aluminum compound and the 2,6-naphthalene-dicarboxylic acid or one of its salts being less than 20% by weight based on the total weight of the reaction mixture.

The organic component of the porous metal-organic framework material of the invention used is 2,6-naphthalenedicarboxylic acid, which can be reacted with an aluminum compound. It is equally possible to use derivatives of 2,6-naphthalenedicarboxylic acid. For instance it is conceivable, for example, that 2,6-naphthalenedicarboxylic acid is used in the form of its salt. The salt in which 2,6-naphthalenedicarboxylic acid is present as completely or partially deprotonated anion can have any suitable cation.

Such cations can be, for example, monovalent or divalent, preferably monovalent, metal ions. Examples of these are, in particular, sodium salts and potassium salts.

Likewise, cations of ammonium compounds can be used. Here, in particular, mention may be made of ammonium itself and also alkylammonium cations.

The aluminum compound can be generated by anodic oxidation of metallic aluminum. In such a case, the porous metal-organic framework material of the invention is produced at least in part by an electrochemical route. Processes for the electrochemical production of porous metal-organic framework materials are described in WO-A 2005/049892. The aluminum compound for the porous metal-organic framework material of the invention can also be generated by this route.

In the electrochemical production of the porous metal-organic framework material of the invention, it is preferred that the cathodic redeposition of the aluminum ion is at least in part prevented by at least one of the following measures:
(i) use of an electrolyte which favors the cathodic formation of hydrogen;
(ii) addition of at least one compound which leads to cathodic depolarization;
(iii) use of a cathode having a suitable hydrogen overvoltage.

The process can be carried out in an undivided electrolysis cell. Especially suitable cells are gap cells or stacked plate cells. These can be connected in a bipolar manner. A suitable reaction medium is, for example, methanol, ethanol, dimethylformamide, diethylformamide or a mixture of two or more of these solvents.

In addition, in the reaction mixture, a supporting electrolyte or a plurality of supporting electrolytes can be present. In this case the supporting electrolyte can have, as cation component, a quaternary ammonium and, as anion component, an alkoxysulfate. The total solids content should be in the range of more than or equal to 0.5% by weight.

The reaction in the process according to the invention for producing the metal-organic framework material of the invention can also proceed by a classical route. In this case the aluminum compound is typically an aluminum salt.

The aluminum salt can be present in the form of alkoxide, acetonate, halide, sulfite, as the salt of an organic or inorganic oxygen-comprising acid or a mixture thereof.

An alkoxide is, for example, a methoxide, ethoxide, n-propoxide, i-propoxide, n-butoxide, i-butoxide, t-butoxide or phenoxide.

An acetonate is, for example, acetylacetonate.

A halide is, for example, chloride, bromide or iodide.

An organic oxygen-comprising acid is, for example, formic acid, acetic acid, propionic acid or other alkylmonocarboxylic acids.

An inorganic oxygen-comprising acid is, for example, sulfuric acid, sulfurous acid, phosphoric acid or nitric acid.

Further preferred aluminum compounds are inorganic aluminum salts such as aluminum chloride, aluminum bromide, aluminum hydrogensulfate, aluminum dihydrogenphosphate, aluminum monohydrogenphosphate, aluminum phosphate, aluminum nitrate.

The aluminum compound can, if appropriate, comprise water of hydration. Preferred aluminum compounds are the hydrates of chloride, nitrate and also sulfate.

The reaction in the process according to the invention for producing the porous metal-organic framework material of the invention proceeds at least in the presence of an organic solvent. In this case, solvothermal conditions can be used. The term "thermal", in the context of the present invention, is taken to mean a production process in which the reaction to give the porous metal-organic framework material of the invention is carried out in a pressure vessel in such a manner that it is closed during the reaction and an elevated temperature is applied so that owing to the vapor pressure of solvent present, a pressure builds up within the reaction medium in the pressure vessel.

Preferably, the reaction does not proceed in an aqueous medium and likewise not under solvothermal conditions.

The reaction in the process of the invention therefore preferably proceeds in the presence of a nonaqueous solvent.

The reaction preferably proceeds at a pressure of at most 2 bar (absolute). Preferably the pressure, however, is at most 1230 mbar (absolute). In particular preferably, the reaction takes place at atmospheric pressure. However, in this case owing to the apparatus, slight overpressures or underpressures can occur. Therefore, in the context of the present invention, the expression "atmospheric pressure" is to be taken to mean that pressure range which is given by the atmospheric pressure actually present ±150 mbar.

The reaction takes place in a temperature range from 100° C. to 200° C. Preferably, the temperature is in the range from 110° C. to 170° C. Further preferably, the temperature is in a range from 120° C. to 150° C.

The reaction mixture can in addition comprise a base. This acts, in particular, in such a manner that when the carboxylic acid is used as at least bidentate organic compound it is readily soluble. By using an organic solvent it is frequently not necessary to use such a base. Nevertheless, the solvent for the process according to the invention can be selected in such a manner that it has a basic reaction as such which, however, need not be obligatory for carrying out the process according to the invention.

Likewise, a base can be added. Preferably, however, no additional base is used.

It is further advantageous that the reaction can take place with stirring, which is also advantageous in the event of scale-up.

(Nonaqueous) organic solvent is preferably a $C_{1-6}$-alkanol, dimethylsulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methyl-pyrrolidone (NMP), gamma-butyrolactone, alicyclic alcohols such as cyclohexanol, ketones such as acetone or acetylacetone, cycloketones such as cyclohexanone, sulfolene or mixtures thereof.

A $C_{1-6}$-alkanol denotes an alcohol having 1 to 6 carbon atoms. Examples of these are methanol, ethanol, n-propanol, isopropanol, n-butanol, isobutanol, t-butanol, pentanol, hexanol and also mixtures thereof.

An optionally halogenated $C_{1-200}$-alkane denotes an alkane having 1 to 200 carbon atoms, wherein one or more up to all hydrogen atoms can be replaced by halogen, preferably chlorine or fluorine, in particular chlorine. Examples thereof are chloroform, dichloromethane, tetrachloromethane, dichloroethane, hexane, heptane, octane and also mixtures thereof.

Preferred solvents are DMF, DEF, DMAc and NMP. Particular preference is given to DMF.

The expression "nonaqueous" preferably relates to a solvent which does not exceed a maximum water content of 10% by weight, more preferably 5% by weight, furthermore preferably 1% by weight, further preferably 0.1% by weight, particularly preferably 0.01% by weight, based on the total weight of the solvent.

Preferably, the maximum water content during the reaction is 10% by weight, more preferably 5% by weight, and furthermore preferably 1% by weight.

The term "solvent" relates to pure solvents and also mixtures of different solvents.

Further preferably, following the process step of reaction of the at least one metal compound with the at least one at least bidentate organic compound is a calcination step. The temperature set in this case is typically above 250° C., preferably 300 to 400° C.

Owing to the calcination step, the at least bidentate organic compound present in the pores can be removed.

Supplementary or alternatively thereto, the removal of the at least bidentate organic compound (ligand) from the pores of the porous metal-organic framework material can proceed via treatment of the resultant framework material with a nonaqueous solvent. In this case the ligand is removed in a type of "extraction process" and if appropriate replaced in the framework material by a solvent molecule.

The treatment proceeds preferably for at least 30 minutes and can typically be carried out for up to 7 days. This can take place at room temperature or elevated temperature. Preferably, it proceeds at elevated temperature, for example, at at least 40° C., preferably 60° C. Further preferably, the extraction takes place at the boiling temperature of the solvent used (under reflux).

The treatment can proceed in a simple vessel by slurrying and stirring the framework material. Use can also be made of extraction apparatuses such as Soxhlet apparatuses, in particular industrial extraction apparatuses.

As suitable solvents, use can be made of the abovementioned, that is, for example, $C_{1-6}$-alkanol, dimethylsulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cycloketones such as cyclohexanone, sulfolene or mixtures thereof.

Preference is given to methanol, ethanol, propanol, acetone, MEK and mixtures thereof.

A very particularly preferred extraction solvent is methanol.

The solvent used for the extraction can be identical to or different from that used for the reaction of the at least one metal compound with the at least one at least bidentate organic compound. In the "extraction" it is not absolutely necessary, but preferred, that the solvent is anhydrous.

After the process according to the invention, the sum of the fractions of the aluminum compound and 2,6-naphthalenedicarboxylic acid or one of its salts ($x_1$) is less than 20% by weight, based on the total weight of the reaction mixture. Preferably, this fraction is less than 15% by weight, in particular less than 12% by weight. This fraction, however, should be greater than 2% by weight, preferably greater than 2.7% by weight.

It is preferred that in the process according to the invention the molar ratio of aluminum compound to 2,6-napthalenedicarboxylic acid or one of its salts ($x_2$) is in the range from 0.3 to 1.5. More preferably, the ratio is in the range from 0.4 to 0.8. A further preferred range for the ratio is the range from 2, in particular from 2.6; the value, however, should not exceed 5.

The present invention further relates to the use of a porous metal-organic framework material according to the invention for taking up at least one substance for its storage, separation, controlled release, chemical reaction, or as support.

Preferably, the at least one substance is a gas or gas mixture.

Processes for storage with the aid of metal-organic framework materials in general are described in WO-A 2005/003622, WO-A 2003/064030, WO-A 2005/049484, WO-A 2006/089908 and also DE-A 10 2005 012 087. The processes described there can also be used for the metal-organic framework material according to the invention.

Processes for separation or purification using metal-organic framework materials in general are described in EP-A 1 674 555, DE-A 10 2005 000938 and in German patent application having the application number DE-A 10 2005 022 844. The processes described there can also be used for the metal-organic framework material according to the invention.

If the porous metal-organic framework material of the invention is used for storage, this preferably proceeds in a temperature range from −200° C. to +80° C. More preference is given to a temperature range of −40° C. to +80° C.

In the context of the present invention, for simplicity the expressions "gas" and "liquid" are used, but here the expression "gas" or "liquid" is likewise to be taken to mean gas mixtures and also liquid mixtures or liquid solutions.

Preferred gases are hydrogen, natural gas, town gas, hydrocarbons, in particular methane, ethane, ethene, acetylene, propane, n-butane and also isobutane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and also xenon.

Particularly preferably, the gas is carbon dioxide which is separated off from a carbon dioxide-comprising gas mixture. Preferably in this case the gas mixture, in addition to carbon dioxide, comprises at least $H_2$, $CH_4$ or carbon monoxide. In particular, the gas mixture, in addition to carbon dioxide, comprises carbon monoxide. Very particular preference is given to mixtures which comprise at least 10% by volume and at most 45% by volume, carbon dioxide and at least 30% by volume, and at most 90% by volume, carbon monoxide.

A preferred embodiment is pressure-swing adsorption having a plurality of parallel adsorber reactors, the adsorbent bed consisting of or comprising the material of the invention. The adsorption phase for the $CO_2$/CO separation preferably takes place at a $CO_2$ partial pressure of 0.6 to 3 bar and a temperature of at least 20° C., but at most 70° C. For desorption of the adsorbed carbon dioxide, the overall pressure in the relevant adsorber reactor is customarily lowered to values between 100 mbar and 1 bar.

Further preference is given to the use of the framework material of the invention for storage of a gas at a minimum pressure of 100 bar (absolute). More preferably, the minimum pressure is 200 bar (absolute), in particular 300 bar (absolute). In this case, particularly preferably, the gas is hydrogen or methane.

However, the at least one substance can also be a liquid. Examples of such a liquid are disinfectants, inorganic or organic solvents, fuels, in particular gasoline or diesel, hydraulic liquid, coolant liquid, brake fluid or an oil, in particular machine oil. In addition, the liquid can be halogenated aliphatic or aromatic, cyclic or acyclic hydrocarbons or mixtures thereof. In particular, the liquid can be acetone, acetonitrile, aniline, anisole, benzene, benzonitrile, bromobenzene, butanol, tert-butanol, quinoline, chlorobenzene, chloroform, cyclohexane, diethylene glycol, diethyl ether, dimethylacetamide, dimethylformamide, dimethylsulfoxide, dioxane, glacial acetic acid, acetic anhydride, ethyl acetate, ethanol, ethylene carbonate, ethylene dichloride, ethylene glycol, ethylene glycol dimethyl ether, formamide, hexane, isopropanol, methanol, methoxypropanol, 3-methyl-1-butanol, methylene chloride, methyl ethyl ketone, N-methylformamide, N-methylpyrrolidone, nitrobenzene, nitromethane, piperidine, propanol, propylene carbonate, pyrridine, carbon disulfide, sulfolane, tetrachloroethene, carbon tetrachloride, tetrahydrofuran, toluene, 1,1,1-trichloroethane, trichloroethylene, triethylamine, triethylene glycol, triglyme, water or mixtures thereof.

In addition, the at least one substance can be an odor substance.

Preferably, the odor substance is a volatile organic or inorganic compound which comprises at least one of the elements nitrogen, phosphorus, oxygen, sulfur, fluorine, chlorine, bromine or iodine or is an unsaturated or aromatic hydrocarbon or a saturated or unsaturated aldehyde or a ketone. More preferred elements are nitrogen, oxygen, phosphorus, sulfur, chlorine, bromine; in particular preference is given to nitrogen, oxygen, phosphorus and sulfur.

In particular, the odor substance is ammonia, hydrogen sulfide, sulfur oxides, nitrogen oxides, ozone, cyclic or acyclic amines, thiols, thioethers and also aldehydes, ketones, esters, ethers, acids or alcohols. Particular preference is given to ammonia, hydrogen sulfide, organic acids (preferably acetic acid, propionic acid, butyric acid, isobutyric acid, valeric acid, isovaleric acid, caproic acid, heptylic acid, lauric acid, pelargonic acid) and also cyclic or acyclic hydrocarbons which comprise nitrogen or sulfur and also saturated or unsaturated aldehydes such as hexanal, heptanal, octanal, nonanal, decanal, octenal or nonenal and, in particular volatile aldehydes, such as butyraldehyde, propionaldehyde, acetaldehyde and formaldehyde, and in addition fuels such as gasoline, diesel (components).

The odor substances can also be fragrances which are used, for example, for production of perfumes. Those which may be mentioned by way of examples as fragrances or oils which release such fragrances are: essential oils, basil oil, geranium oil, mint oil, cananga tree oil, cardamon oil, lavender oil, peppermint oil, muskat oil, camomile oil, eucalyptus oil, rosemary oil, lemon oil, lime oil, orange oil, bergamot oil, dalmation-type sage oil, coriander oil, cypress oil, 1,1-dimethoxy-2-phenylethane, 2,4-dimethyl-4-phenyltetrahydrofuran, dimethyltetrahydrobenzaldehyde, 2,6-dimethyl-7-octen-2-ol, 1,2-diethoxy-3,7-dimethyl-2,6-octadiene, phenylacetaldehyde, rose oxide, ethyl 2-methylpentanoate, 1-(2,6,6-trimethyl-1,3-cyclohexadien-1-yl)-2-buten-1-one, ethylvanillin, 2,6-dimethyl-2-octenol, 3,7-dimethyl-2-octenol, tert-butylcyclohexyl acetate, anisyl acetates, allyl cyclohexyloxyacetate, ethyllinalool, eugenol, coumarin, ethyl acetoacetate, 4-phenyl-2,4,6-trimethyl-1,3-dioxane, 4-methylene-3,5,6,6-tetramethyl-2-heptanone, ethyltetrahydrosafranate, geranylnitrile, cis-3-hexen-1-ol, cis-3-hexenyl acetate, cis-3-hexenyl methyl carboantes, 2,6-dimethyl-5-hepten-1-al, 4-(tricyclo[5.2.1.0]decylidene)-8-butanal, 5-(2,2,3-trimethy1-3-cyclopentenyl)-3-methylpentan-2-ol, p-tert-butyl-alpha-methylhydrocinnamaldehyde, ethyl[5.2.1.0]-tricyclodecanecarboxylate, geraniol, citronellol, citral, linalool, linalyl acetate, ionones, phenylethanol or mixtures thereof In the context of the present invention, a volatile odor substance preferably has a boiling point or boiling range of below 300° C. More preferably, the odor substance is a readily volatile compound or mixture. In particular preferably, the odor substance has a boiling point or boiling range of below 250° C., more preferably below 230° C., in particular preferably below 200° C.

Preference is likewise given to odor substances which have a high volatility. As a measure of volatility, the vapor pressure can be used. In the context of the present invention, a volatile odor substance preferably has a vapor pressure of greater than 0.001 kPa (20° C.). More preferably, the odor substance is a readily volatile compound or mixture. In particular preferably, the odor substance has a vapor pressure of greater than 0.01 kPa (20° C.), more preferably a vapor pressure of greater than 0.05 kPa (20° C.). Particularly preferably, the odor substances have a vapor pressure of greater than 0.1 kPa (20° C.).

Examples in which a chemical reaction can take place in the presence of the metal-organic framework material of the invention are the alkoxylation of monools and also of polyols. The procedure of such alkoxylations is described in WO-A 03/035717 and also WO-A 2005/03069. Likewise, the porous metal-organic framework material of the invention can be used for epoxidation and also for production of polyalkylene carbonates and hydrogen peroxide. Such reactions are described in WO-A 03/101975, WO-A 2004/037895 and also US-A 2004/081611.

Particular preference is given to catalytic reactions.

In addition, the metal-organic framework material of the invention can serve as support, in particular as a support of a catalyst.

EXAMPLES

Example 1

Production of an Al-2,6-naphthalenedicarboxylic acid Metal-organic Framework Material (Al-NDC) According to the Invention 5 g of $AlCl_3 \cdot 6H_2O$ and 6.72 g of 2,6-naphthalenedicarboxylic acid (molar ratio: Al:linker ratio, x2,=0.66) are suspended in a glass flask in 300 ml of DMF (sum of the starting material fractions to total weight of the reaction mixture in % by weight, x1, 3.9) and stirred for 17 h under reflux (130° C.). The resultant solid is filtered off and washed with 3×50 ml of DMF and 4×50 ml of methanol. Subsequently the substance is dried in a vacuum drying cabinet at 110° C. for 20 h. This produces 6.89 g of a white intermediate. The $N_2$ surface area is determined at 269 $m^2/g$ (Langmuir).

1.71 g of the intermediate are extracted with boiling methanol for 4 days in an extraction apparatus. Subsequently the product (1.09 g) is dried for 16 h at 150° C. in a vacuum drying cabinet. This product has a specific Langmuir surface area of 1988 $m^2/g$. The XRD is shown in FIG. 1. In this case, in the diffractogram, as also in the remaining diffractograms, I denotes the intensity (Lin (counts)) and 2Θ the 2-theta scale.

Figure 6:
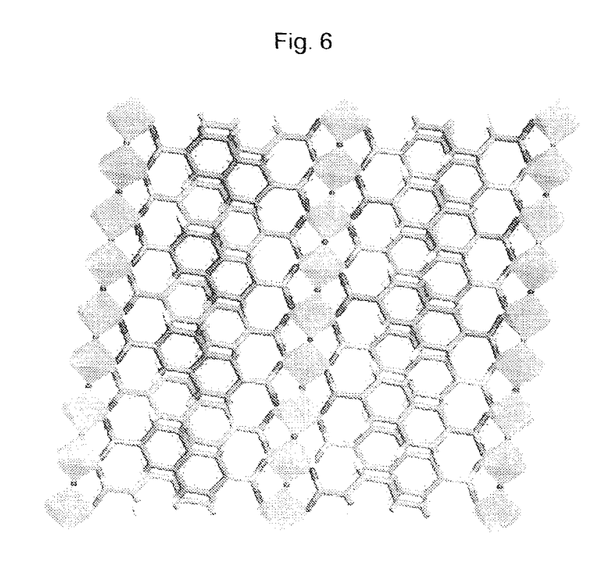
FIG. 6 shows a proposed structure (plane a,c)
Figure 7:
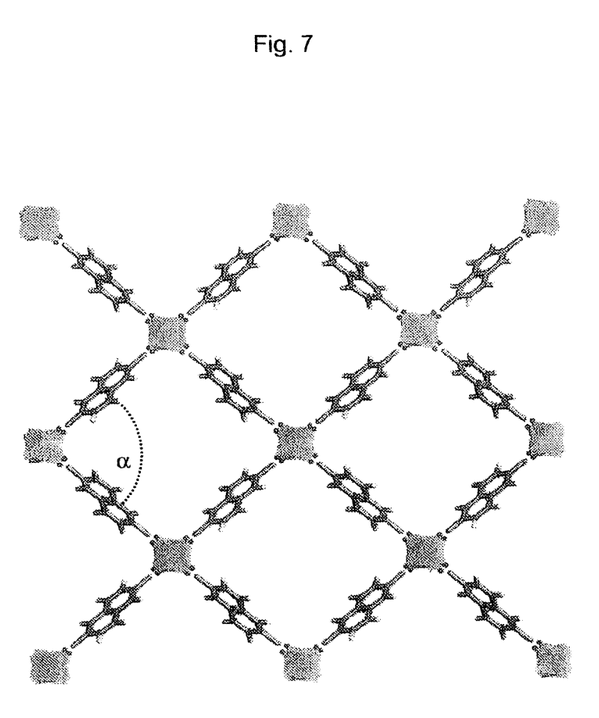
FIG. 7 shows a proposed structure (plane a,b).

A structure proposal is shown in FIGS. 6 (plane a, c) and 7 (plane a, b). This is an orthorhombic structure. The aperture angle α in this structure is 82.5° (compared with approximately 35° for MIL-69).

Starting from the structure known in the prior art, a scan of the b vector of the Al-NDC cell is carried out from 14 to 18 Å in 0.5 Å steps. All other cell parameters (a, b, c) and the molecular structure are optimized with respect to each b value within the C2c space group, with the "OFF force field", as was implemented in the Cerius program, being transformed. The XRD patterns at each of the reoptimized scan points were generated using the "Reflex powder diffraction" module of the software package Materials Studio V2.1 (Acceloys Inc., San Diego, US).

The resultant XRD patterns are compared with the experimentally obtained XRD structure by superimposition and the suitable range for the x axis is selected. The y axis is then rescaled in such a manner that it agrees with the intensities of the strongest reflection.

On this basis, initially it is found visually that the structure having "b"=18 Å best correlates with the experimental data. Nevertheless, all structures having values in the range from 18 to 16.5 Å agree well with the experimental values owing to the relatively broad reflection.

This permits a certain margin for the choice of a suitable b length. When both positions of the reflections and intensities are taken in accoutnt, this results in the fact that a structure having a b vector of 16.5 Å in length best agrees with the experimental XRD. Structures having values less than 16.5 Å for b shift in the direction of high theta values, with the intensity and positions no longer agreeing. All these structures can be ignored as possible solutions.

The structures which are obtained with the "permitted" b length ranges correspond to the following internal Al—Al—Al angles (compared with the experimental values of MIL-69* and the ht, or as*, structures of aluminum terephthalate):

| b (Å) | Angle (Al—Al—Al) |
| --- | --- |
| 18.0 | 90 |
| 17.5 | 87 |
| 17.0 | 84 |
| 16.5 | 81 |
| 7.53 | 35* |
|  | 71** |
|  | 75*** |

This comparison shows that not only the cell dimension but also the internal structure of the framework materials of the invention differ from those of the prior art. In the novel structure, channel structures which are more open may be found compared with those from the prior art.

On the basis of the agreement of the positions of the reflections and intensity between experimental XRD patterns and simulation patterns, the following structure is proposed as a very probable structure having the following coordinates:

| Space group | C2c | | |
|---|---|---|---|
| a | 19.38570 | alpha | 90.0 |
| b | 16.500000 | beta | 90.0 |
| c | 6.11620 | gamma | 101.6 |
| Fractional coordinates | | | |
| Atom | a | b | c |
| O | 0.06478 | −0.92638 | 0.60817 |
| O | 0.06785 | −0.93013 | 0.97876 |
| C | 0.14628 | −0.84122 | 0.84478 |
| C | 0.19227 | −0.83455 | 0.05343 |
| C | 0.29301 | 0.77063 | 0.29415 |
| C | 0.08982 | −0.90275 | 0.80853 |
| C | 0.24629 | −0.77654 | 0.08763 |
| C | 0.34566 | −0.71153 | 0.32867 |
| H | 0.31342 | −0.37510 | 0.31175 |
| H | 1.28863 | −0.18852 | −1.07063 |
| H | 2.38077 | −0.29217 | −1.00960 |
| Al | 0.00000 | 0.00000 | 0.00000 |
| O | 0.00000 | −0.03397 | 0.75000 |

This is the theoretically simulated structure which agrees best with the experimentally determined XRD pattern and also shows a minimum for the scanned potential energy surface. However, a further structure is also found having a minimum near this structure (b=18), with its parameters being listed hereinafter, despite the lower agreement:

| Space group | C2c | | |
|---|---|---|---|
| a | 17.99800 | alpha | 90.0 |
| b | 18.00000 | beta | 90.0 |
| c | 6.11610 | gamma | 101.7 |
| Fractional coordinates | | | |
| Atom | a | b | c |
| O | 0.06942 | −0.93200 | 0.60934 |
| O | 0.07288 | −0.93525 | 0.98028 |
| C | 0.15102 | −0.84750 | 0.84396 |
| C | 0.19865 | −0.83551 | 0.05439 |
| C | 0.29732 | 0.76340 | 0.29709 |
| C | 0.09525 | −0.90894 | 0.80963 |
| C | 0.24903 | −0.77499 | 0.08855 |
| C | 0.34605 | −0.70216 | 0.33147 |
| H | 0.30339 | −0.37327 | 0.30879 |
| H | 1.29741 | −0.19830 | −1.06623 |
| H | 2.38290 | −0.30529 | −1.00569 |
| Al | 0.00000 | 0.00000 | 0.00000 |
| O | 0.00000 | −0.03093 | 0.75000 |

Comparative Example 1

Production of an Al-NDC-MOF ("MIL-69")

15.31 g of Al(NO$_3$)$_3$.9H$_2$O and 15.04 g of 2,6-naphthalene-dicarboxylic acid (×2=0.58) are suspended in 102 g of DMF (×1=29) in a glass flask and kept at 170° C. for 24 h in a Berghoff autoclave ("Teflon liner"). The resultant solid is filtered off and washed with 2×50 ml of DMF and 3×100 ml of methanol. Subsequently the substance is dried in a vacuum drying cabinet at 200° C. for 5 h. Thereafter the intermediate is extracted under reflux in a large excess of methanol for several hours, filtered off and washed repeatedly with methanol and again dried for 5 h at 200° C. in a vacuum drying cabinet. A white product is obtained having an N$_2$ surface area of only 230 m$^2$/g (Langmuir). The XRD is shown in FIG. 2. On the basis of the position of reflections, the product can be identified as the "MIL-69" phase known from the literature.

Comparative Example 2

Production not According to the Invention of a Mixture of Framework Material Al-NDC According to the Invention and Known Framework Material Al-NDC 59.2 g of AlCl$_3$.6H$_2$O and 90.3 g of 2,6-naphthalenedicarboxylic acid (×2=0.59) are suspended in 645 ml of DMF (×1=23) in a glass flask and stirred for 17 h under reflux (130° C.). The resultant solid is filtered off and washed with 2×150 ml of DMF and 4×150 ml of methanol. Subsequently, the substance is dried in a vacuum drying cabinet at 110° C. for 16 h. Thereafter the intermediate is extracted under reflux in a large excess of methanol for several hours, filtered off and washed repeatedly with methanol and again dried for 16 h at 110° C. in a vacuum drying cabinet. A white product is obtained having an N$_2$ surface area of only 510 m$^3$/g (Langmuir). The XRD is shown in FIG. 3. This is thought to be a mixture of the structure according to the invention and MIL-69.

Example 2

Hydrogen Isotherms at 77 K (Storage of Hydrogen)

Figure 4:
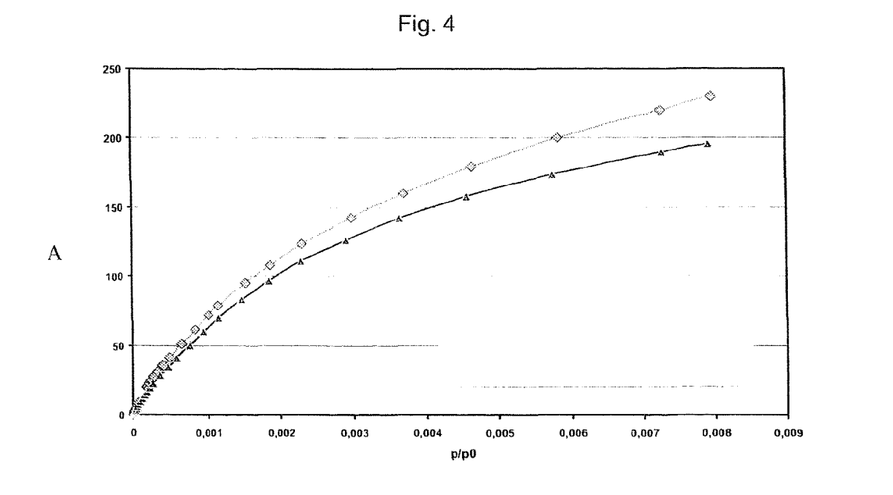
FIG. 4 shows a comparison of the $H_2$ uptake A as a function of the relative pressure.

FIG. 4 shows the comparison of the H$_2$ uptake A (ml/g) as a function of the relative pressure p/p0. Measurements are made on a commercially available Quantachrome instrument having the name Autosorb-1. The measurement temperature is 77.4 K. The samples, before measurement, are each pretreated in vacuum for 4 h at room temperature and subsequently for a further 4 h at 200° C.

The upper curve in FIG. 4 shows the H$_2$ uptake on the framework material from example 1. The lower curve relates to Al terephthalate which is produced in accordance with example 1 of DE-A 10 2005 39 623 and which, after the precipitation, was extracted with methanol in a similar manner to the above example 1 instead of being calcined.

Example 3

Production of a Framework Material According to the Invention 10 g of AlCl$_3$.6H$_2$O and 13.44 g of 2,6-naphthalenedicarboxylic acid (x2 =0.66) are suspended in 600 ml of DMF in a glass flask (×1=3.9) and stirred for 17 h under reflux (130° C.). The resultant solid is filtered off and washed repeatedly with acetone. Thereafter the intermediate is extracted under reflux in great excess of methanol for several hours, filtered off and washed repeatedly with methanol. Subsequently the substance is dried in a vacuum drying cabinet at 110° C. for 16 h. 11.5 g of a white intermediate are obtained. This product has an N$_2$ surface area of 2085 m$^2$/g (Langmuir). The XRD is similar to that from example 1.

Example 4

Suitability for CO$_2$ Separations

Pure substance isotherms of CO$_2$ and CO are recorded on the material from example 3 at 42° C. (FIG. 5).

Figure 5:
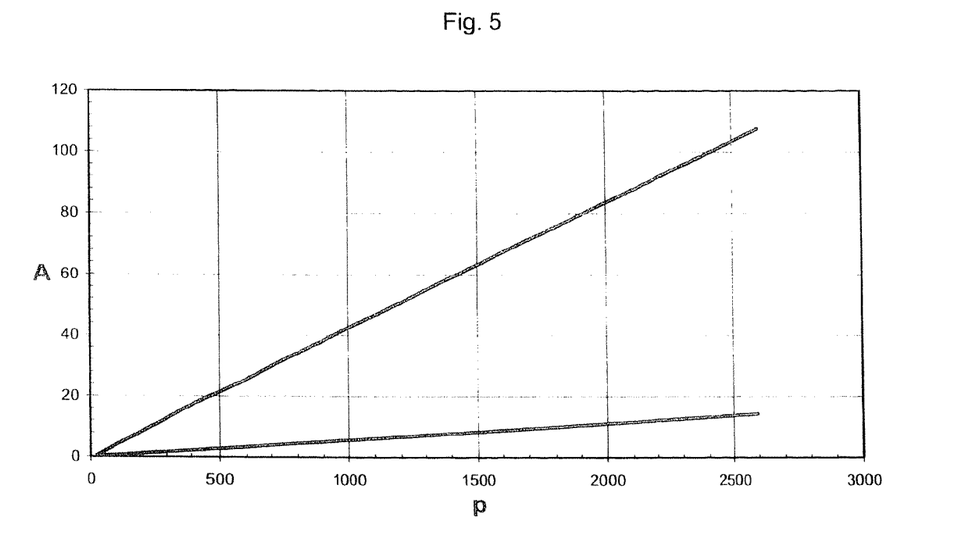
FIG. 5 shows pure substance isotherms of CO2 and CO recorded on the material from example 3.

In FIG. 5, the upper curve shows the adsorbed amount A (mg/g) of carbon dioxide at 42° C., and the lower curve that of carbon monoxide, in each case as a function of the absolute pressure (mbar). On the basis of the markedly differing curve position, the framework material of the invention is suitable in principle for separating $CO_2$ from gas mixtures which in addition comprise carbon monoxide.

Example 5

Production of the Framework Material of the Invention 7.5 g of $AlCl_3.6H_2O$ and 10 g of 2,6-naphthalenedicarboxylic acid (×2=0.66) are suspended in 300 ml of DMF in a glass flask (×1=5.8) and stirred under reflux (130° C.) for 17 h. The resultant solid is filtered off and washed with 2×50 ml of DMF and 4×50 ml of methanol. Subsequently the substance is dried in a vacuum drying cabinet at 110° C. for 16 h. Thereafter the intermediate is extracted under reflux in a large excess of methanol for several hours, filtered off and washed repeatedly with methanol and again dried for 16 h at 110° C. in a vacuum drying cabinet. A white product having an $N_2$ surface area of 1866 $m^2$/g (Langmuir) is obtained. The XRD is similar to that from example 1.

Example 6

Production of the Framework Material of the Invention 15 g of $AlCl_3.6H_2O$ and 5 g of 2,6-naphthalenedicarboxylic acid (×2=2.66) are suspended in 300 ml of DMF in a glass flask (×1=6.6) and stirred under reflux (130° C.) for 17 h. The resultant solid is filtered off and washed with 2×50 ml of DMF and 4×50 ml of methanol. Subsequently the substance is dried in a vacuum drying cabinet at 110° C. for 16 h. Thereafter the intermediate is extracted under reflux in a large excess of methanol for several hours, filtered off and washed repeatedly with methanol and again dried for 16 h at 110° C. in a vacuum drying cabinet. A white product having an $N_2$ surface area of 1517 $m^2$/g (Langmuir) is obtained. The XRD is similar to that from example 1.

Example 7

Production of the Framework Material of the Invention 1.25 g of $AlCl_3.6H_2O$ and 1.64 g of 2,6-naphthalenedicarboxylic acid (×2 =0.66) are suspended in 142 ml of DMF in a glass flask (×1=2) and kept at 170° C. for 24 h in a Berghoff autoclave ("Teflon liner"). The resultant solid is filtered off and washed with 2×50 ml of DMF and 4×50 ml of methanol. Subsequently the substance is dried in a vacuum drying cabinet at 110° C. for 16 h. Thereafter the intermediate is extracted under reflux in a large excess of methanol for several hours, filtered off and washed repeatedly with methanol and again dried for 16 h at 110° C. in a vacuum drying cabinet. A white product having an $N_2$ surface area of only 1005 $m^2$/g (Langmuir) is obtained. The XRD is similar to FIG. 1, but very poorly crystalline.

Example 8

Production of the Framework Material of the Invention 120.72 g of $AlCl_3.6H_2O$ and 183.76 g of 2,6-naphthalenedicarboxylic acid (×2=0.59) are suspended in 2400 ml of DMF in a glass flask (×1=12.7) and stirred for 17 h at 130° C. under reflux. The resultant solid is filtered off and washed with 3×400 ml of DMF and 3×400 ml of methanol. Thereafter the intermediate is extracted under reflux in 2.5 l of methanol for 24 h, filtered off and washed repeatedly with methanol. Subsequently the substance is dried in a vacuum drying cabinet for 24 h at 100° C. A white product is obtained having an $N_2$ surface area of 1465 $m^2$/g (Langmuir).

Example 9

Production of the Framework Material of the Invention 181.07 g of $AlCl_3.6H_2O$ and 275.64 g of 2,6-naphthalenedicarboxylic acid (×2=0.59) are suspended in 5000 ml of DMF in a glass flask (×1=9.1) and stirred under reflux for 17 h at 130° C. The resultant solid is filtered off and washed with 3×400 ml of DMF and 3×400 ml of methanol. Thereafter the intermediate is extracted under reflux for 24 hours in 2.5 l of methanol, filtered off and washed repeatedly with methanol. Subsequently the substance is dried in a vacuum drying cabinet at 100° C. for 24 h. 198 g of white product are obtained having an $N_2$ surface area of 2019 $m^2$/g (Langmuir).

This invention claimed is:

1. A porous metal-organic framework material comprising a bidentate organic compound bound by coordination to a metal ion, wherein
   the metal ion is $Al^{III}$ and the bidentate organic compound being is 2,6-naphthalenedicarboxylate
   wherein said metal-organic frameworks materal is prepared by reacting a reaction mixture comprising an aluminum compound, 2,6-naphthalenedicarboxylic acid or one of its salts and an organic solvent comprising N,N-dimethylformamide at temperatures in the range from 100° C. to 200° C. by stirring, wherein the sum of the fractions of the aluminum compound and the 2,6-naphthalenedicarboxylic acid or one of its salts is less than 20% by weight based on the total weight of the reaction mixture,
   a X-ray diffractogram (XRD) of the framework material has a first reflection in the range from $6.5°<2\Theta<7.5°$ and a second reflection in the range from $13.8°<2\Theta<15.0°$,
   the area of the first reflection is greatest in relation to the area of all reflections in the range from $2°<2\Theta<70°$,
   the area of the second reflection is second greatest, and
   the sum of the areas of the first and second reflections is at least 50% of the total area of all reflections in the range from $2°<2\Theta<70°$ and wherein the framework material, as powder, has a specific surface area of at least 1,000 $m^2$/g determined according to Langmuir by $N_2$ adsorption at 77K.

2. The porous metal-organic framework material according to claim 1, wherein the first reflection is in the range from $6.7°<2\Theta<7.3°$ and the second reflection is in the range from $13.9°<2\Theta<14.8°$.

3. The porous metal-organic framework material according to claim 1, wherein the framework material, as powder, has a specific surface area of at least 1000 $m^2$/g determined according to Langmuir by $N_2$ adsorption at 77 K.

4. The porous metal-organic framework material according to claim 1, wherein pores in said material are present in the form of one-dimensional channels having a diameter of greater than 10 but less than 25 Å.

5. The porous metal-organic framework material according to claim 1, wherein pores in said material are present in the form of one-dimensional channels having a diameter of from 15 to 20 Å.

6. The porous metal-organic framework material according to claim 1, wherein pores in said material are present in the form of one-dimensional channels having a diameter of from 16 to 18 Å.

7. The porous metal-organic framework material according to claim 1, wherein said framework material, as powder, has a specific surface area of at least 1,200 m²/g.

8. The porous metal-organic framework material according to claim 1, wherein said framework material, as powder, has a specific surface area of at least 1,400 m²/g.

9. The porous metal-organic framework material according to claim 1, wherein said framework material, as powder, has a specific surface area of at least 1,600 m²/g.

10. The porous metal-organic framework material according to claim 1, wherein said framework material, as powder, has a specific surface area of at least 1,800 m²/g.

11. A shaped body comprising a porous metal-organic framework material according to claim 1.

12. The shaped body according to claim 11, wherein the shaped body has a specific surface area of at least 1,200 m²/g determined according to Langmuir by $N_2$ adsorption at 77 K.

13. A process for producing the porous metal-organic framework material according to claim 1 comprising: reacting a reaction mixture comprising an aluminum compound, 2,6-naphthalenedicarboxylic acid or one of its salts and an organic solvent comprising N,N-demethylformamide at temperatures in the range from 100° C. to 200° C. by stirring, wherein the sum of the fractions of the aluminum compound and the 2,6-naphthalenedicarboxylic acid or one of its salts being is less than 20% by weight based on the total weight of the reaction mixture.

14. The process according to claim 13, wherein the molar ratio of aluminum compound to 2,6-naphthalenedicarboxylic acid or one of its salts is in the range from 0.3 to 1.5.

15. A method for the storage, separation, controlled release, chemical reaction or support of at least one substance, comprising receiving said at least one substance by the metal-organic framework material according to claim 1.

16. The method according to claim 15, wherein said at least one substance is carbon dioxide in order to separate said carbon dioxide from a carbon dioxide-containing gas mixture.

17. The method according to claim 15, wherein said at least one substance is a gas in order to store said gas at a minimum pressure of 100 bar (absolute).

* * * * *